(12) United States Patent
Koh

(10) Patent No.: US 7,225,016 B1
(45) Date of Patent: May 29, 2007

(54) IMPLANTABLE MEDICAL DEVICE WITH NERVE SIGNAL SENSING

(75) Inventor: Steve Koh, South Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 367 days.

(21) Appl. No.: 10/870,367

(22) Filed: Jun. 16, 2004

(51) Int. Cl.
*A61N 1/04* (2006.01)
*A61N 1/37* (2006.01)
*A61B 5/04* (2006.01)

(52) U.S. Cl. .................... 607/2; 607/3; 607/4; 607/42; 607/48; 607/118; 600/544; 600/546

(58) Field of Classification Search ............... 607/2–6, 607/42, 48, 118, 62; 600/544, 546, 554, 600/557
See application file for complete search history.

(56) References Cited

U.S. PATENT DOCUMENTS

| 4,432,375 A | * | 2/1984 | Angel et al. ............... 600/518 |
| 4,830,008 A | * | 5/1989 | Meer ........................... 607/42 |
| 5,483,969 A | | 1/1996 | Testerman et al. .......... 128/716 |
| 5,485,851 A | | 1/1996 | Erickson ..................... 128/716 |
| 5,540,733 A | | 7/1996 | Testerman et al. ............ 607/42 |
| 6,415,183 B1 | * | 7/2002 | Scheiner et al. ............... 607/42 |

FOREIGN PATENT DOCUMENTS

| EP | 0505195 A2 | 9/1992 |
| EP | 0505195 A3 | 9/1992 |
| EP | 0505195 B1 | 9/1992 |

OTHER PUBLICATIONS

Janis Kelly, "New Method Permits Neural Control of Mechanical Ventilation," Pulmonary Reviews.com, vol. 5, No. 5 (May 2000), 4 pages.

* cited by examiner

*Primary Examiner*—Robert Pezzuto
*Assistant Examiner*—Shevon Johnson

(57) ABSTRACT

An implantable medical device which has a sensor that provides a waveform to an energy accumulator, such as a capacitor. The waveform is representative of electrical activity from a nerve. The implantable medical device further includes a threshold detector which provides a discrete output signal when the energy in the signal energy accumulator exceeds a threshold. The signal energy accumulator can be periodically discharged and then recharged during the time period that electrical activity is being sensed from the nerve thereby generating a number of discrete output signals each time the recharged energy accumulator exceeds the threshold. The frequency and number of pulsed outputs is indicative of the sensed electrical activity.

20 Claims, 8 Drawing Sheets

NERVE SIGNAL

PULSE OUTPUT

RECONSTRUCTED NERVE SIGNAL

IMPLANTABLE MEDICAL DEVICE WITH NERVE SIGNAL SENSING

FIELD OF THE INVENTION

The invention relates to implantable medical devices that sense electrical impulses propagated along nerves and which may provide therapy accordingly.

BACKGROUND OF THE INVENTION

Central sleep apnea (CSA) is a condition characterized by periodic temporary cessation of normal respiration. Central sleep apnea is differentiated from other categories of apneas, such as obstructive sleep apnea, by having a neurological rather than a structural origin. In episodes of CSA, nerve stimulation to the diaphragm temporarily decreases to the point that the afflicted person's diaphragm fails to properly contract thus failing to inspire. As the person's metabolism proceeds leading to an increasing metabolic need for respiration, the person becomes partially aroused interrupting the apneic episode with respiration. The respiration immediately following an apneic episode frequently is of hyperventilatory nature and recurrent episodes of CSA and hyperventilation disrupts the person's restful sleep. Alternating episodes of CSA and hyperventilation and consequent swings in sympathetic drive are also found in patients experiencing some degree of heart failure (HF) and these episodes of CSA, in addition to being disruptive of the patient's sleep, also tend to worsen the persons HF. Thus, it will be appreciated that there is a need for detection and therapeutic treatment for patients suffering from CSA.

As CSA involves a temporary cessation of normal respiration, one method of detecting CSA is to observe the patient's respiration and detect an occurrence of an excessive delay of the initiation of an inspiration cycle. For example, an impedance sensor arranged to measure the patient's transthoracic impedance can measure the cyclic variations in the transthoracic impedance as the lungs are filled and emptied through the breathing cycle. Sensors can also be arranged about the patient's thorax to detect the expansion and contraction of the chest cavity throughout the respiration cycle. However, these methods actually measure the patient's respiratory response rather than the driving neurological demand and are somewhat susceptible to erroneous measurements, for example due to patient movement during sleep. The phrenic nerves conduct respiratory demand signals from the brain to the left and right sides of the diaphragm and sensing activity on the phrenic nerves could provide the ability to directly sense the patient's respiratory demand rather than inferring this demand based on measurements of the respiratory response.

Sensing phrenic nerve signals are known in some implantable medical device applications. For example, U.S. Pat. No. 5,483,969 to Testerman et al. discloses a system for measuring phrenic nerve activity in order to apply appropriate sleep apnea therapy. However, the manner in which known implantable medical devices monitor nerve activity, such as phrenic nerve activity, is generally not conducive for use in many implantable medical device applications, particularly those intended for long-term implantation. In particular, in order to accurately assess nerve signals, band pass filtering and relatively high-rate sampling, such as on the order of 30 kHz, must typically be performed to accurately sense the signals. However, when the implantable medical device relies upon battery power, the use of such high-rate sampling may excessively draw on the battery and have the effect of significantly limiting the useful life of the implantable medical device before battery replacement is indicated.

Hence, there is a need for an implantable medical device that is capable of monitoring nerve activity so that the implantable medical device is better able to assess neurologically determined parameters affecting treatment afforded to patients. To this end, there is a need for a system and method that is able to accurately sense signals in a patient's nervous system in a manner that consumes less battery power.

SUMMARY

The aforementioned needs are satisfied by an implantable medical device that has leads adapted to provide stimulation therapy to tissue of the patient. The implantable medical device, in this aspect, includes a nerve sensor which detects electrical activity within a selected nerve and develops a waveform that corresponds to the electrical signal within the selected nerve.

In one specific implementation, the implantable medical device further includes an accumulator element that accumulates the energy of the waveform representative of the nerve signal and, when accumulated energy exceeds a particular threshold, a threshold signal indicative of the threshold being exceeded is produced. The implantable medical device further includes a controller, which controls the delivery of therapeutic stimulation to the tissue of the patient and receives the threshold signal. The controller, by evaluating one or more characteristics of the threshold signal, for example the occurrence frequency of the threshold signal over a preselected time period, can then determine characteristics of the sensed nerve signal. Hence, in this particular aspect, the invention is capable of detecting and evaluating the signal within a particular nerve without engaging in band pass filtering or high frequency sampling.

In one particular implementation, the implantable medical device comprises an implantable cardiac stimulation device, such as a pacemaker or ICD. The nerve sensor can sense electrical activity of the phrenic nerve so as to get an indication of the intrinsically or neurologically determined respiration and corresponding metabolic need of the patient.

In one particular implementation, the signal energy accumulator element comprises a capacitor device and further comprises a comparator and a one-shot component such that, when the energy accumulated in the capacitor exceeds the threshold, the comparator provides a pulsed output indicative of the capacitor charge exceeding the threshold.

In one particular implementation, the pulsed output controls a gate structure which thereby reduces the accumulated charge on the capacitor. Hence, by reducing the charge stored in the capacitor, subsequent energy provided by the waveform corresponding to the sensed nerve signal can then be recharged to the capacitor. By evaluating the number of pulses or the intervals between pulses during a set time period, the duration and/or magnitude of the phrenic nerve signal can be approximated.

Hence, in these implementations, the system allows for evaluation of nerve activities in a manner that does not significantly consume limited battery capability. These and other objects and advantages will become more apparent from the following description taken in conjunction with the accompanying drawings.

DETAILED DESCRIPTION OF THE PREFERRED EMBODIMENT

Reference will now be made to the drawings wherein like numerals refer to like parts throughout. The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
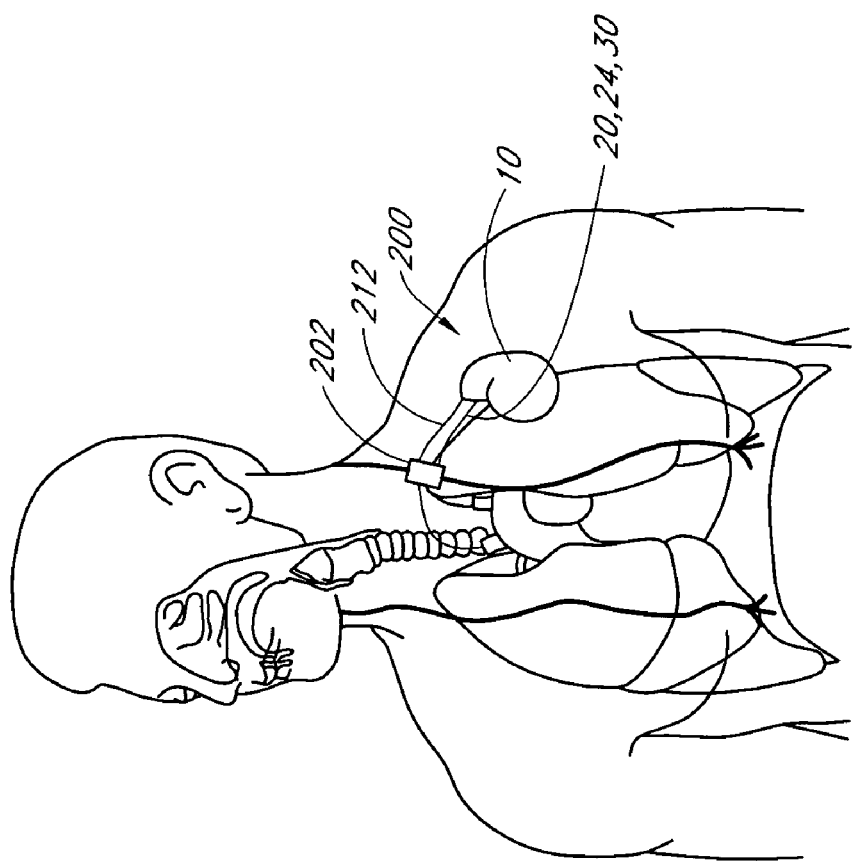
FIG. 1 illustrates one embodiment of an implantable nerve sensing system which includes a nerve sensing component such as a nerve electrode assembly.

FIG. 1 illustrates a patient provided with a nerve sensing system 200. The nerve sensing system 200 is adapted to accurately sense nerve activity, such as activity on the phrenic nerves, in an efficient manner which reduces power consumption during nerve sensing. The nerve sensing system 200 comprises one or more nerve electrode assemblies 202 which either inductively or by direct contact with the nerve sense signals therefrom.

Figure 2:
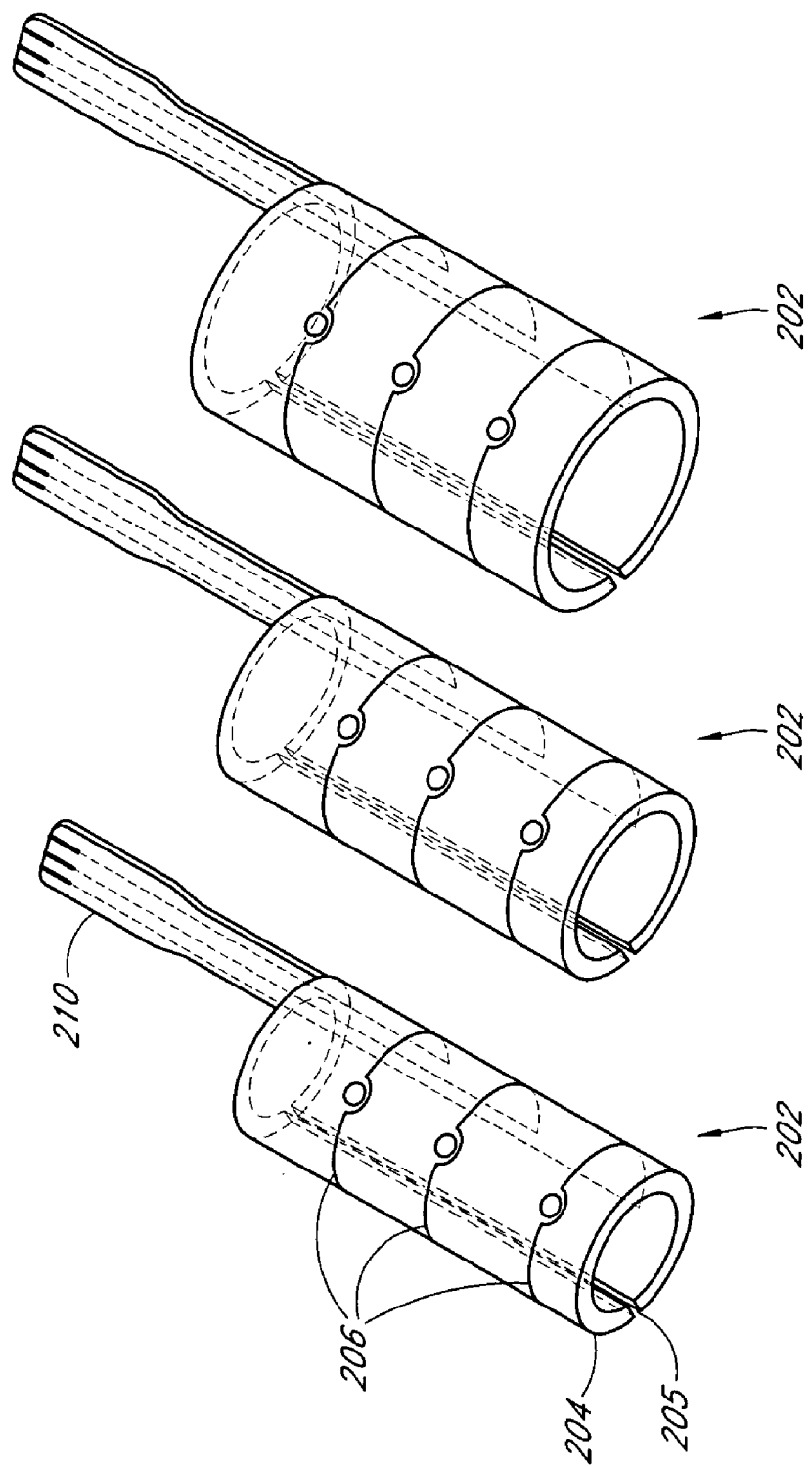
FIG. 2 is a perspective view of various sizes of one embodiment of nerve electrode assemblies forming part of the implantable nerve sensing system of FIG. 1.

FIG. 2 illustrates one embodiment of nerve electrode assembly 202 in great detail. In the embodiment illustrated in FIG. 2, three different sizes of nerve electrode assemblies 202 are shown which are sized and configured for sensing from nerves of various sizes. In this embodiment, the nerve electrode assemblies 202 comprise a flexible sleeve 204 which retains and supports one or more electrodes 206. In this embodiment, the nerve electrode assembly 202 comprises three separate electrodes 206 which are arranged to extend substantially circumferentially about a nerve positioned within the nerve electrode assembly 202. The electrodes 206 are also spaced apart from each other in a substantially equidistant manner and can thus provide the functionality as desired depending upon the particular application of sensing the direction of propagation of signals along the nerve as well as to provide the capability of both sensing and stimulating the nerve via the multiple separate electrodes 206. The nerve electrode assembly 202 also comprises a connector 210 in electrical communication with the electrodes 206 and wherein the connector 210 is configured for connection to a lead 212 (FIG. 1).

In this embodiment, the nerve electrode assembly 202 comprises biocompatible materials which are also selected or suitably coated to reduce the susceptibility to corrosion during the implantation period. In this embodiment, the flexible sleeve 204 is also configured as a generally hollow cylindrical or tubular structure with a substantially axially extending slit or opening 205 extending substantially the length of the nerve electrode assembly 202. The flexible sleeve 204 and electrodes 206 are also comprised of a flexible material such that the nerve electrode assembly 202 can be splayed open along the slit or opening 205, wrapped around a nerve which is positioned within the nerve electrode assembly, and secured thereto, such as via suturing, stapling, and/or biocompatible adhesives. In certain embodiments, the flexible sleeve 204 comprises a flexible and resilient material such that the nerve electrode assembly 202 can be splayed open and wrapped around a nerve such that, upon release, the nerve electrode assembly 202 resiliently bears on the nerve for attachment. It will be appreciated that the materials, sizes, configurations and attachment of the nerve electrode assemblies 202 as well as the connection to and arrangement of the lead 212 is preferably selected to avoid application of undue pressure or stress to the nerve to avoid injury or degradation of function.

The nerve sensing system 200 also comprises an implantable medical device 10 referred to hereafter as "device 10" for brevity which is provided with signals sensed from the nerve by the one or more electrodes 206, the connector 210 and lead 212. The device 10 processes these nerve activity signals for analysis, storage, and/or determination of therapy delivery as described in greater detail below.

Figure 3:
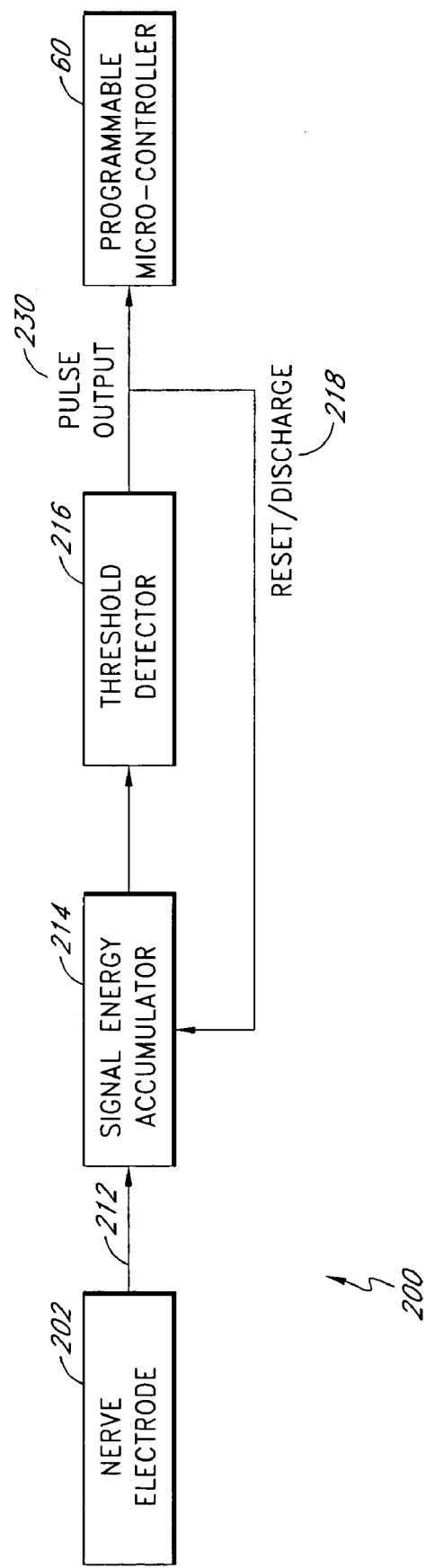
FIG. 3 is a functional block diagram of the nerve sensing system of FIG. 1.

FIG. 3 is a block diagram which illustrates signal analysis components of the nerve sensing system 200 which, in this embodiment, are embodied within the device 10. In this particular implementation, the nerve sensing system 200 includes a signal energy accumulator 214 which receives nerve signals from the nerve electrode assembly 202 and lead 212. Thus, the magnitude and duration of the waveform provided to the signal energy accumulator 214 corresponds to the magnitude and duration of the signal that the patient's brain is providing to the muscles of the patient's diaphragm via the phrenic nerves.

As will be discussed in greater detail below, the signal energy accumulator 214 accumulates energy, in this embodiment electrical charge, from the waveform being supplied by the nerve electrode assembly 202. Hence, the accumulated energy or charge within the accumulator 214 is indicative of the magnitude and duration of the waveform from the nerve electrode assembly 202 which, in turn, corresponds to the magnitude and duration of the signal being sent by the brain to the diaphragm via the phrenic nerves.

As is further illustrated in FIG. 3, the nerve sensing system 200 includes a threshold detector 216 that monitors the accumulated energy in the signal energy accumulator 214. The threshold detector 216 is configured to provide a pulsed output 230 each time the accumulated energy within the signal energy accumulator 214 exceeds a predefined threshold which in certain embodiments is adjustable.

The pulsed output 230 can then be supplied to a programmable microcontroller 60 of the device 10 and the programmable microcontroller 60 can make an assessment of the magnitude and duration of the nerve signal(s) by evaluating the characteristics of the pulsed outputs 230. The manner in which the programmable microcontroller 60 can make an assessment or determination of the strength and duration of the activity in the nerve will be described in greater detail below in connection with FIGS. 5A–5D and 6.

In this embodiment, a reset/discharge 218 is also performed with the provision of the pulsed output 230. The reset/discharge 218 partially dissipates or drains the energy accumulated in the signal energy accumulator 214. The signal energy accumulator 214 then continues to re-accumulate additional signal energy corresponding to the nerve activity, recharging the energy removed by the reset/discharge 218. Cycles of continued monitoring of the accumulated energy by the threshold detector 216 with generation of the pulsed output 230 and reset/discharge 218 at intervals that would generally vary over time with the intensity or strength of the nerve activity would thus occur.

Figure 4:
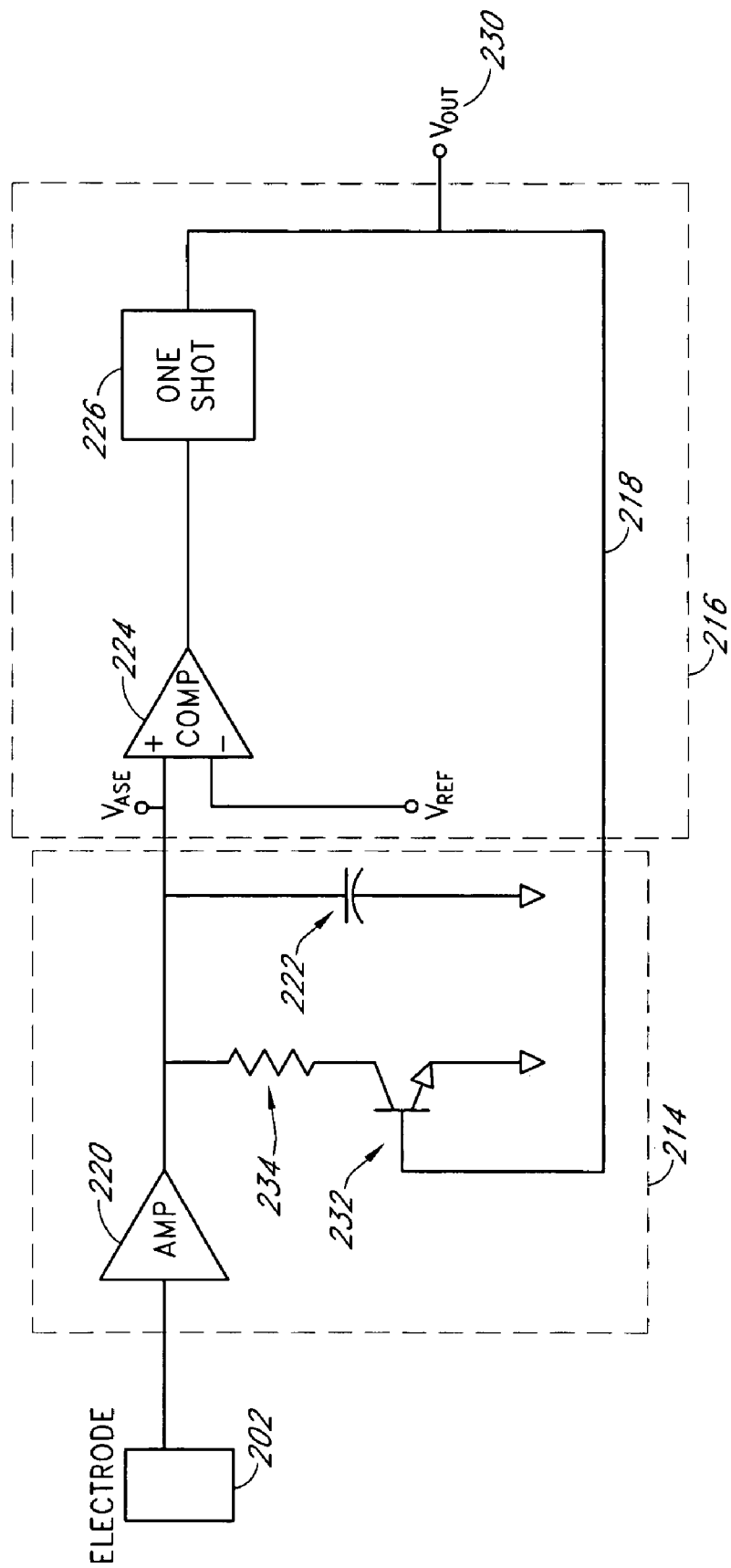
FIG. 4 is a circuit diagram in greater detail of a signal energy accumulator and threshold detector blocks of the nerve sensing system of FIGS. 1 and 3.

FIG. 4 is a circuit diagram which illustrates in greater detail one embodiment of signal analysis components of the nerve sensing system 200. As is shown in FIG. 4, the nerve electrode assembly 202 provides electrical signals sensed from the nerve as a waveform that is provided via an amplifier 220 to a capacitor 222. As the waveform is provided to the capacitor 222, charge builds up in the capacitor 222 so as to provide an accumulated signal energy voltage $V_{ASE}$ to a comparator 224.

The accumulated signal energy voltage $V_{ASE}$ on the capacitor 222 is compared to a threshold voltage $V_{REF}$ by the comparator 224. In one embodiment, the threshold voltage $V_{REF}$ is fixed at a pre-selected value. In other embodiments, the threshold voltage $V_{REF}$ is adjustable or programmable. When the voltage in the capacitor 222 exceeds the threshold $V_{REF}$, the comparator 224 provides an output signal to a one-shot device 226 which then develops a pulsed output $V_{OUT}$ 230. In this embodiment, the pulsed output 230 is provided to the programmable microcontroller 60.

In this particular implementation, the pulsed output 230 is also provided to the gate or base of a transistor 232 which is coupled to the capacitor 222 via a resistor 234. Hence, each time the voltage in the capacitor 222 exceeds the threshold $V_{REF}$, the transistor 232 is enabled thereby briefly connecting the capacitor 222 to ground and thereby partially draining the capacitor 222 for the reset/discharge 218. In this embodiment, the pulsed output 230 and reset/discharge 218 occur in a one-to-one correspondence and substantially simultaneously, however in other embodiments, the pulsed output 230 and reset/discharge 218 may lack a one-to-one correspondence and/or can be phase shifted with respect to each other. In this embodiment, the parameters of the pulsed output 230 and reset/discharge 218, such as magnitude and pulse width, are selected such that the capacitor 222 is drained slightly below $V_{REF}$ by enablement of the transistor 232 such that, assuming continuing provision of nerve signal energy by the nerve electrode assembly 202 and lead 212, the accumulated signal energy voltage $V_{ASE}$ describes generally a saw-tooth waveform oscillating generally slightly below and up to $V_{REF}$. The slopes and periods of the $V_{ASE}$ waveform will depend on the characteristics of the sensed nerve activity and component values of the nerve sensing system 200.

In this way, as the waveform indicative of the nerve signal is provided by the nerve electrode assembly 202, a pulsed output 230 is provided each time the accumulated nerve signal energy exceeds the threshold value V. When the threshold is exceeded, the capacitor 222 is partially discharged thereby allowing the waveform to successively build-up charge in the capacitor 222 and successively deliver pulsed outputs 230. By varying the threshold voltage $V_{REF}$, the granularity or resolution of the nerve sensing system 200 can be adjusted such that the pulsed outputs 230 correspond to a greater or lesser accumulated signal energy. Thus, the threshold voltage $V_{REF}$ can be adjusted such that a fewer or greater number (longer or shorter interval) of pulsed outputs 230 are provided for a given level of nerve signal strength. By suitable selection of $V_{REF}$ and component values, the nerve sensing system 200 can achieve desired resolution of nerve sensing without the significant energy consumption of high-rate sampling to achieve comparable resolution, thus significantly extending the functionality of the implantable device 10 with reduced burden on battery power.

As previously described, the number or interval between (or frequency of) pulsed outputs 230 provided to the microcontroller 60 over the time period that the nerve sensing system 200 is detecting activity within the nerve of interest is indicative of the strength and duration of the nerve activity. In particular, the higher the amplitude of the nerve signal, the quicker the capacitor 222 develops a voltage $V_{ASE}$ that exceeds the threshold $V_{REF}$. Similarly, the longer the duration of the nerve signal, the more times the capacitor 222 will develop the voltage $V_{ASE}$ that exceeds $V_{REF}$ and will thus produce more pulsed output 230 signals. Hence, the interval between/frequency with which the pulsed outputs 230 are provided is indicative of the strength of the nerve signal and the time period over which the pulsed output 230 is provided is indicative of the duration of the nerve signal. These represent two separate parameters of the nerve signal that can be captured and evaluated by the device 10 of the nerve sensing system 200 in an energy efficient manner.

Figure 5A:
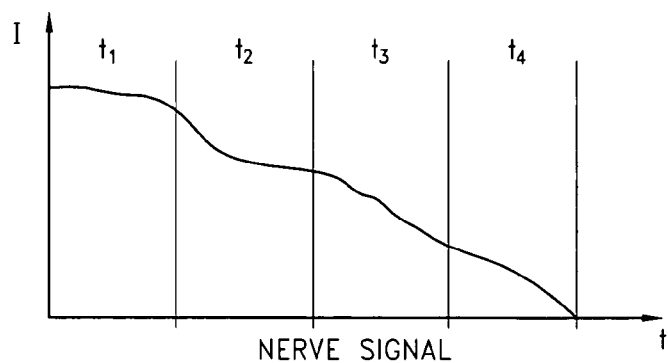
FIGS. 5A–5D are waveforms illustrating a sensed nerve signal, the output from the signal energy accumulator and threshold detector, a reconstructed nerve signal corresponding to output pulse counts over sensing time periods, and the intervals between output pulses as determined by the programmable microcontroller of the implantable nerve sensing system of FIG. 1, respectively.
Figure 5B:
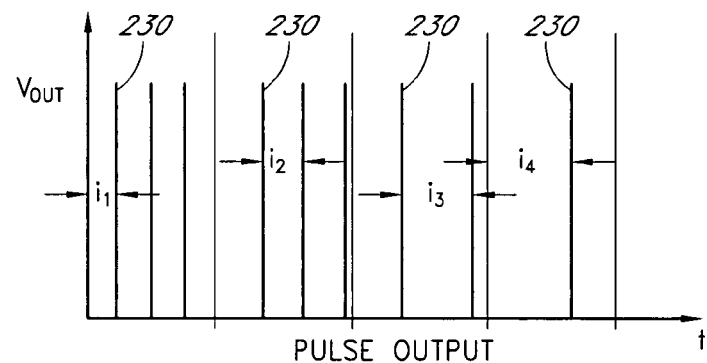

FIGS. 5A–5D graphically illustrate the operation of embodiments of the nerve sensing system 200 in greater detail. FIG. 5A is a simplified representation of a period of a nerve activity, such as a phrenic nerve activity signal. In this particular implementation, the nerve activity is being sensed by the nerve electrode 202 which sends a corresponding waveform to the signal energy accumulator 214. During a first time period $T_1$, which can be any of a number of selected durations, e.g. 50 ms, 100 ms, etc. either fixed or adjustable, the capacitor 222 successively develops sufficient accumulated charge to generate four pulsed outputs 230 at intervals of $i_1$ as illustrated by FIG. 5B. During a subsequent time period $T_2$, the nerve signal decreases in amplitude, which means that the capacitor 222 will charge to a voltage greater than $V_{REF}$ less frequently resulting in only three pulsed outputs 230 at longer intervals of $i_2$ being provided by the comparator 224 and the one-shot 226.

Figure 5C:
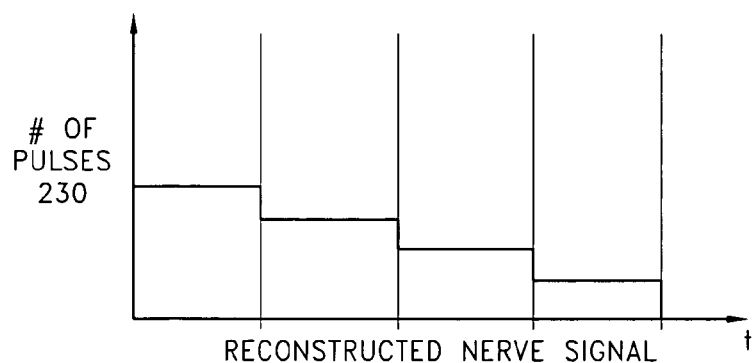
Figure 5D:
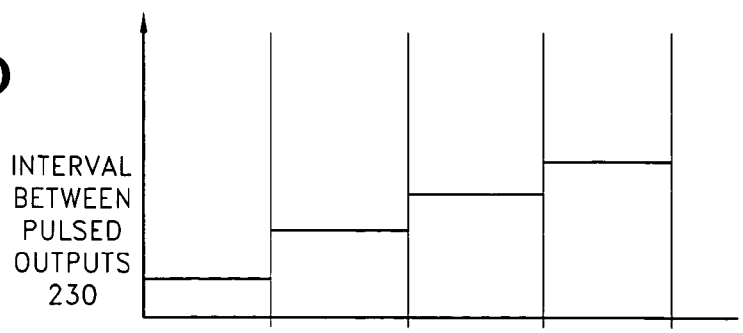

Similarly, during time periods $T_3$ and $T_4$, the number of pulsed outputs 230 further declines and the corresponding intervals $i_3$ and $i_4$ increase as the nerve activity signal energy being provided to the capacitor 222 from the nerve electrode assembly 202 is declining. As is illustrated in FIG. 5C, by plotting the number of pulsed outputs 230 occurring during a given period of time, e.g., $T_1$–$T_4$, a representation of the nerve activity can be reconstructed by the programmable microcontroller 60. Similarly, as illustrated in FIG. 5D, the intervals $i_1$–$i_4$ between the pulsed outputs 230 can also be evaluated as complementary indicators of the level of nerve activity Hence, the nerve sensing system 200 illustrated herein is capable of providing signals to the programmable microcontroller 60 corresponding to sensed nerve activity, such as phrenic nerve activity which is indicative of determined physiologic activity of the patient. This information can then be used by the implantable medical device 10 in order to more accurately assess the patient's condition as well as to adapt therapy to improve the performance of the implantable medical device 10. For example, by detecting the intrinsic neurologically determined respiratory demand of the patient via observation of phrenic nerve activity, the implantable cardiac stimulation device 10 can monitor for episodes of CSA. The device 10 can store this information for internal analysis, can transmit the information to an external device for remote analysis, as well as use the information for determination of therapy delivery.

As a result of using a capacitor or similar device to accumulate signal energy and then providing pulsed output when the accumulated energy exceeds a preselected threshold, information about the nerve activity strength and duration can be captured and provided to the programmable microcontroller 60 without requiring high-rate sampling or filtering devices which are relatively demanding of battery capacity. As such, this information can be provided to the programmable microcontroller 60 with a reduced drain on limited battery power.

Figure 6:
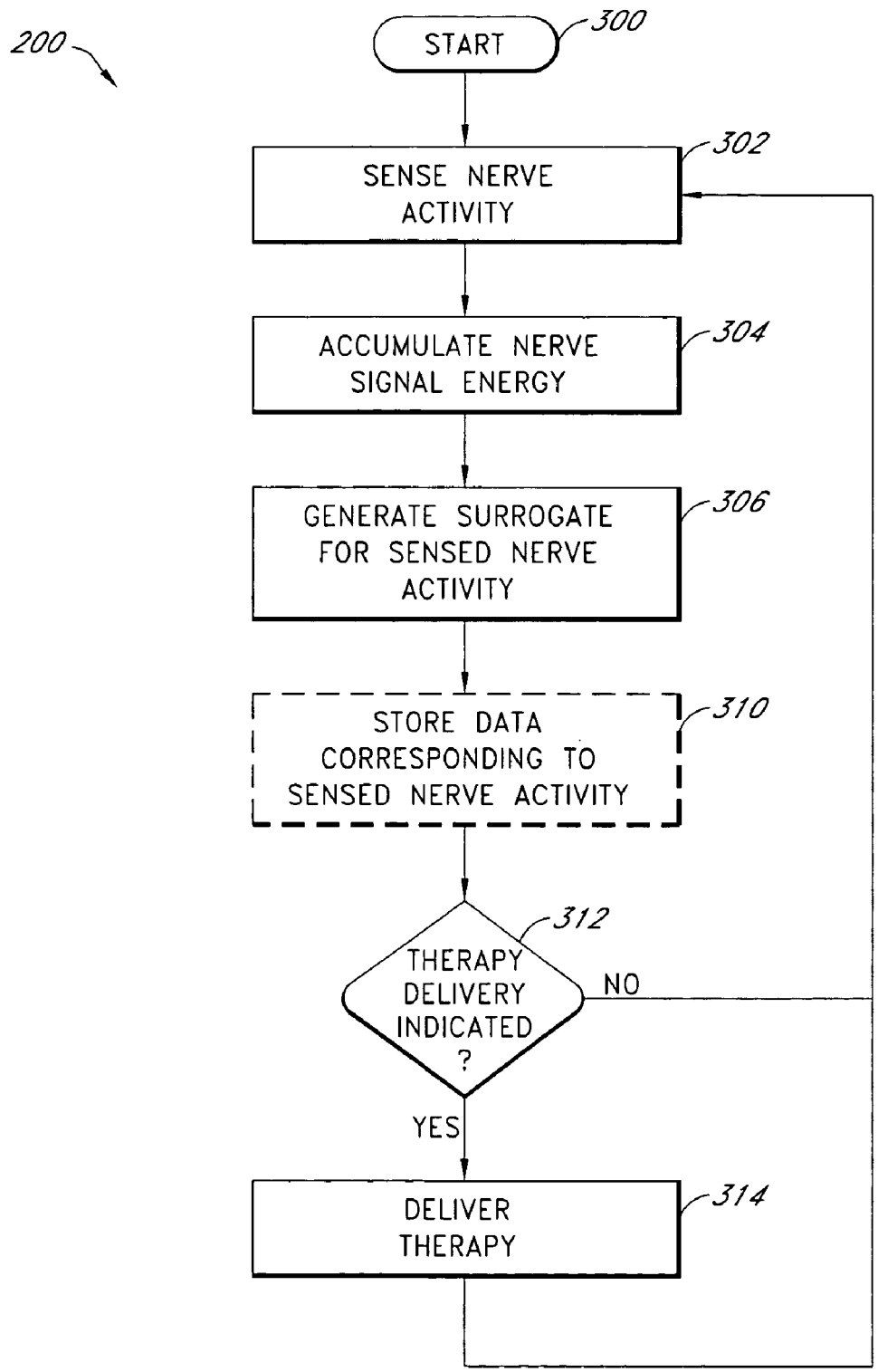
FIG. 6 is a flow chart of embodiments of nerve sensing, analysis, and delivery of indicated therapy, which may include nerve stimulation.

In certain embodiments, the device 10 analyzes the information developed by the nerve sensing system 200 to improve the delivery of therapy by the device 10. FIG. 6 is a flow chart illustrating one embodiment of this aspect. From a start state 300 which can include attachment and connection of one or more nerve electrode assemblies 202 with the connector 210 and lead 212 to the device 10 as previously described follows a state 302 where the nerve activity is sensed also as previously described. A state 304 follows where the nerve activity signal energy is accumulated by the signal energy accumulator 214. Following in state 306, a surrogate is generated for the sensed nerve activity, such as the pulsed outputs 230 as previously described.

An optional state 310 can follow where data corresponding to the sensed nerve activity is stored. This storage of data in state 310 can be utilized by the device 10 for internal analysis of the patient's condition. The storage of data in state 310 can also be utilized for subsequent transmission to an external device for remote analysis of the internally sensed nerve activity. It will be appreciated that in various embodiments, the storage of data in state 310 can comprise storage of raw data, running and/or periodic averages, histograms, etc. depending upon the requirements of specific applications.

A decision state 312 follows where a determination is made whether the sensed nerve activity indicates delivery of therapy. For example, as previously described the nerve sensing system 200 can sense activity on the phrenic nerves and thus the decision of state 312 can comprise, in certain embodiments, a determination as to whether or not a period of CSA has occurred. Similarly, in other embodiments, the determination of state 312 can comprise an evaluation of observed phrenic nerve activity indicative of the patient's respiratory demand and corresponding metabolic need. In these embodiments, the determination of state 312 can be utilized to more closely match cardiac pacing to the patient's observed respiratory demand in a rate responsive manner.

If the determination of state 312 is positive, e.g. that delivery of therapy is indicated, this therapy is provided in state 314.

In one embodiment, the therapy provided in state 314 can comprise CSA therapy and include stimulation provided to the phrenic nerves by the nerve electrode assemblies 202. In one particular embodiment, a modulated pulse train of approximately one volt and of 10–40 Hz is provided in state 314 to stimulate the diaphragm for inspiration. In other embodiments, the therapy provided in state 314 can comprise direct stimulation of muscle tissue, such as the diaphragm, or stimulation of other nerves, such as the vagus nerve. The processes performed by the nerve sensing system 200 as illustrated in the flow chart of FIG. 6 would generally be ongoing throughout the implantation period and thus following either a negative decision of state 312 or an affirmative decision of state 312 with subsequent delivery of therapy in state 314, the sensing and processing of states 302, 304, 306, and evaluation of state 312 would be an ongoing process.

Figure 7:
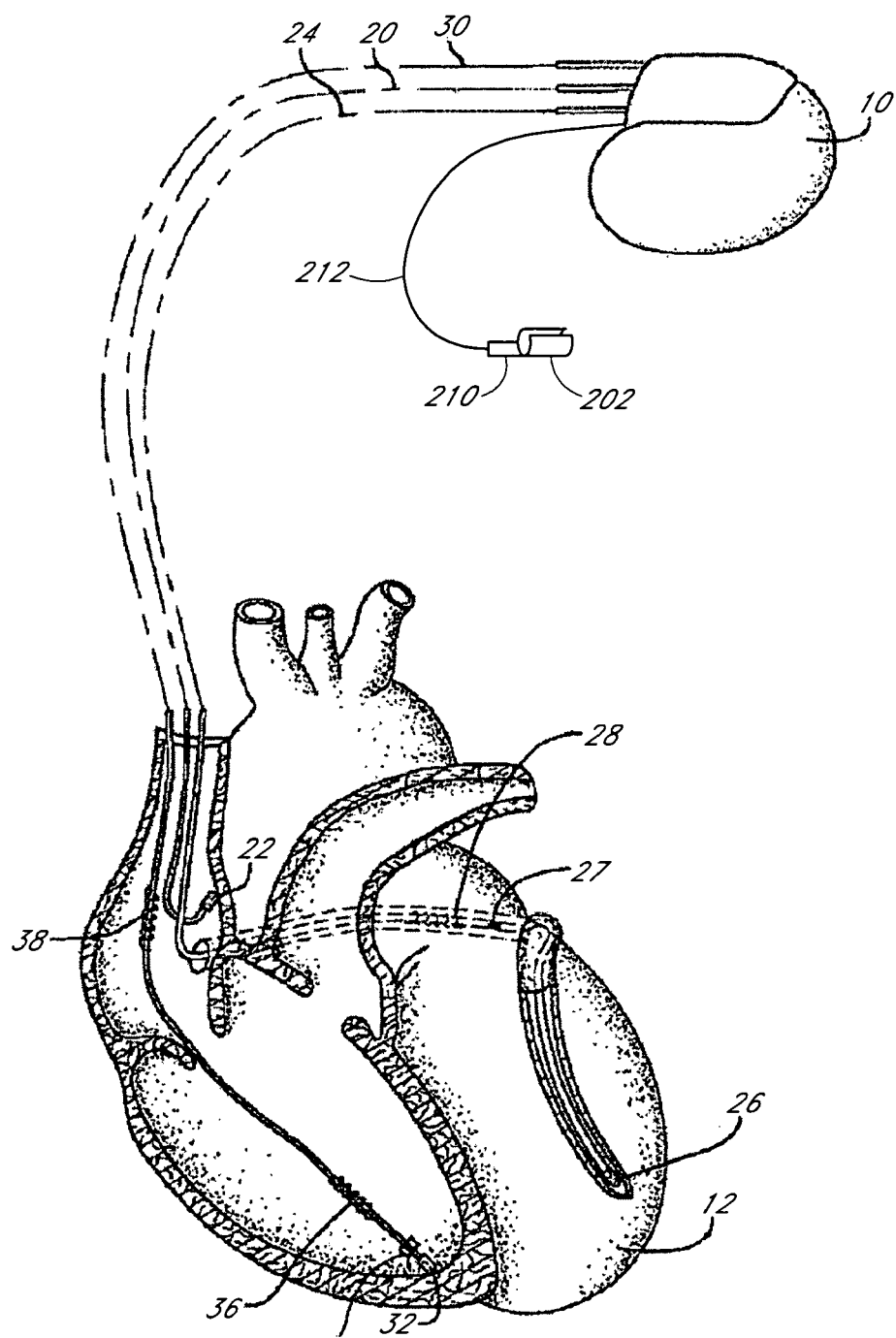
FIG. 7 is a simplified diagram illustrating an implantable stimulation device in electrical communication with at least three leads implanted into a patient's heart for delivering multi-chamber stimulation and shock therapy.

In one embodiment, as shown in FIGS. 1 and 7, the device 10 comprises an implantable cardiac stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium (OS) for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 8:
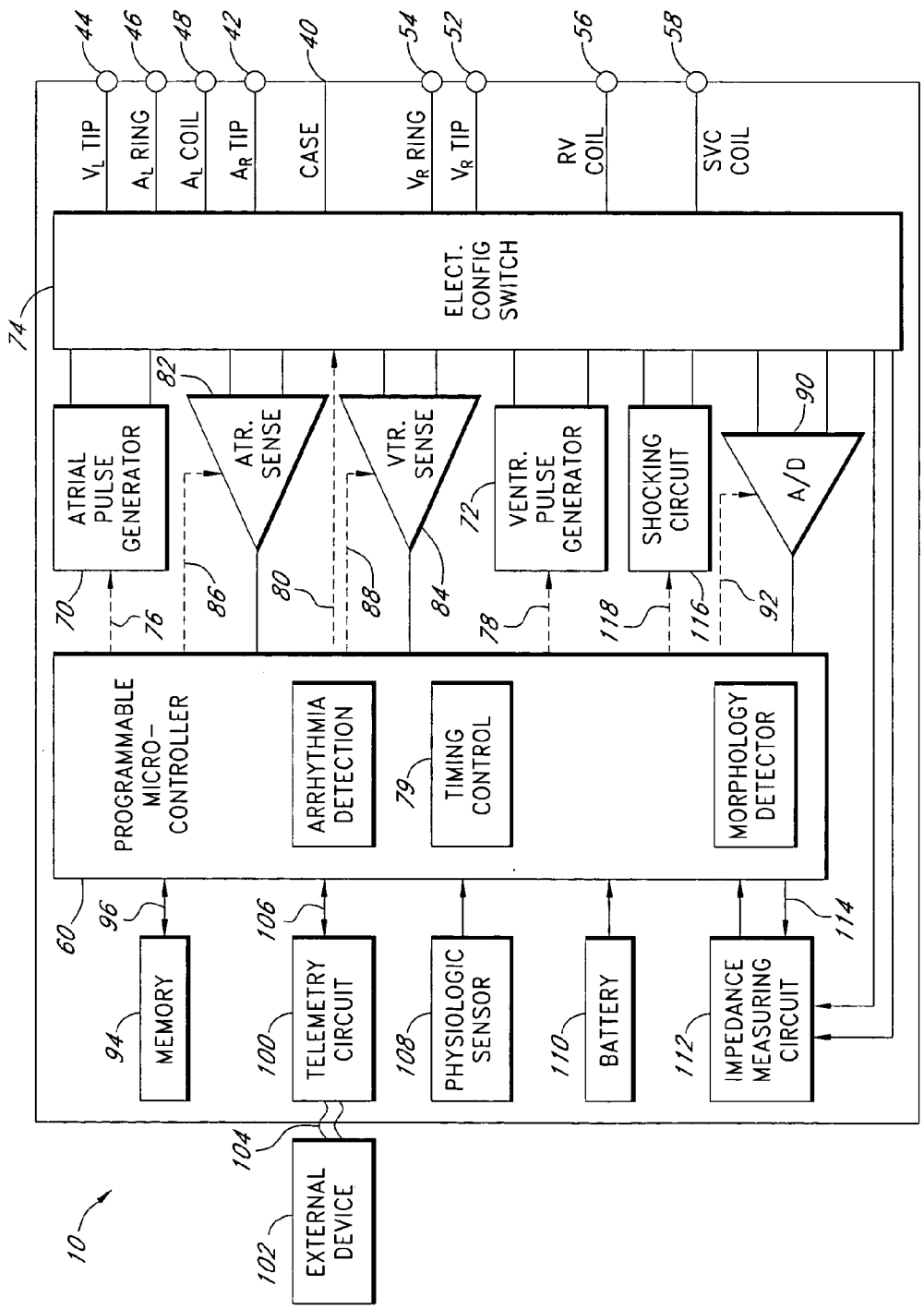
FIG. 8 is a functional block diagram of a multi-chamber implantable stimulation device illustrating the basic elements of a stimulation device which can provide cardioversion, defibrillation and pacing stimulation in four chambers of the heart.

As illustrated in FIG. 8, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 8, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art.

As shown in FIG. 8, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independently of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses. In this embodiment, the physiologic sensor 108 comprises the nerve sensing system 200 such that the device 10 is provided information related to nerve activity such that the device 10 can adjust delivery of therapy, such as CSA or pacing therapy, in state 314.

The stimulation device additionally includes a battery 110 which provides operating power to all of the circuits shown in FIG. 8. For the stimulation device 10, which employs shocking therapy, the battery 110 must be capable of operating at low current drains for long periods of time and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices.

As further shown in FIG. 8, the device 10 is shown as having an impedance measuring circuit 112 which is enabled by the microcontroller 60 via a control signal 114.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Thus, in certain embodiments, the nerve sensing system 200 monitors nerve activity to improve delivery of therapy, such as pacing therapy that is not necessarily directly related to the observed nerve activity. In other embodiments, the nerve sensing system 200 also monitors nerve activity and provides therapy, such as overdrive pacing to the heart 12, as therapy for conditions such as CSA to attempt to restore more desirable activity patterns for the observed nerve, such as the phrenic nerves. In yet other embodiments, the nerve sensing system 200 monitors nerve activity and provides, when indicated, therapy to the observed nerve and/or corresponding enervated tissue to supplement an observed deficiency in the nerve activity.

Although the above disclosed embodiments of the present teachings have shown, described and pointed out the fundamental novel features of the invention as applied to the above-disclosed embodiments, it should be understood that various omissions, substitutions, and changes in the form of the detail of the devices, systems and/or methods illustrated may be made by those skilled in the art without departing from the scope of the present teachings. Consequently, the scope of the invention should not be limited to the foregoing description but should be defined by the appended claims.

What is claimed is:

1. An implantable medical device adapted to be implanted within a patient, the device comprising:
   a nerve sensing system that senses the duration and magnitude of an electrical signal from a nerve of the patient and accumulates energy therefrom, wherein the nerve sensing system is programmed to:
   i) compare the accumulated energy to a threshold;
   ii) when the accumulated energy exceeds the threshold, provide an output signal;
   iii) when the accumulated energy exceeds the threshold, partially dissipate the accumulated energy; and
   iv) repeat steps i)–iii) as the electrical signal is sensed from the nerve.

2. The device of claim 1, wherein the nerve sensing system includes a nerve sensing component that couples to the nerve such that electrical activity from the nerve is provided to the nerve sensing system.

3. The device of claim 2, wherein the nerve sensing component comprises an electrode assembly that is adapted to be positioned about the nerve so as to be electrically coupled therewith.

4. The device of claim 3, wherein the electrode assembly is in electrical contact with the surface of the nerve.

5. The device of claim 1, wherein the nerve sensing system accumulates nerve signal energy in a capacitor.

6. The device of claim 1, wherein the nerve sensing system further comprises a threshold detector and a one-shot device in communication with the threshold detector such that the one-shot device provides a pulsed output signal when the accumulated energy exceeds the threshold.

7. The device of claim 6, wherein the threshold detector comprises a comparator.

8. The device of claim 6, wherein the threshold is adjustable to provide adjustable nerve sensing resolution by varying the characteristics of the pulsed output.

9. The device of claim 6, further comprising a gated dissipation component wherein the gated dissipation component partially dissipates the accumulated energy when the one-shot device provides the output signal such that the nerve signal energy is successively accumulated and discharged while the nerve sensing system is sensing the nerve signal to thereby provide a plurality of output signals indicative of the magnitude and duration of the nerve signal.

10. The device of claim 9, wherein the gated dissipation component comprises a transistor coupled to a capacitor so as to provide a gated path to ground and wherein the gate of the transistor receives a signal to enable the transistor when the one-shot device provides an output signal.

11. The device of claim 1, further comprising a controller receiving the output signals so as to perform at least one of storage and analysis of the output signals.

12. The device of claim 11, further comprising:
a stimulation pulse generator; and
at least one lead with at least one stimulation electrode operably connected to the stimulation pulse generator wherein the controller evaluates the output signals and, upon determination that the output signals indicate delivery of therapy, induces the stimulation pulse generator and at least one lead with at least one stimulation electrode to deliver an appropriate stimulation to the patient.

13. The device of claim 12, wherein the nerve sensing system is arranged to sense phrenic nerve activity and wherein the controller evaluates the output signals for indications of central sleep apnea and, upon determination that an episode of central sleep apnea has occurred, induces the stimulation pulse generator and at least one lead with at least one electrode to provide appropriate stimulation to the patient's diaphragm.

14. The device of claim 13, wherein the appropriate stimulation is provided to the patient's diaphragm via application of stimulation to a phrenic nerve.

15. An implantable stimulation device adapted to be implanted within a patient so as to provide therapeutic stimulation to a patient, the device comprising:
means for delivering therapeutic electrical stimulation to the patient;
means for sensing and storing energy from activity of a selected nerve of the patient's body;
means for consecutively partially dissipating the energy stored by the means for sensing and storing wherein the means for dissipating provides an output signal indicative of the nerve activity; and
means for controlling delivery of therapeutic electrical stimulation to the patient, wherein the means for control uses the output signal to adjust the delivery of the therapeutic electrical stimulation to the patient.

16. The device of claim 15, wherein the means for sensing and storing includes an electrode assembly that is coupled to the nerve and a signal energy accumulator that receives energy from the electrode assembly so as to accumulate energy at a rate corresponding to the magnitude and duration of the electrical signal from the nerve.

17. The device of claim 15, wherein the means for dissipating provides the output signal as a series of pulses wherein the interval between output pulses corresponds to the magnitude of the nerve activity.

18. The device of claim 15, wherein the means for control monitors for indications of central sleep apnea (CSA) and, upon indication of an episode of CSA, induces the means for delivering stimulation to deliver an appropriate stimulation.

19. The device of claim 18, wherein the means for delivering stimulation comprises an electrode coupled to a phrenic nerve and wherein the appropriate stimulation comprises electrical stimulations applied to the phrenic nerve.

20. The device of claim 15, wherein the means for delivering stimulation and the means for sensing and storing commonly comprise an electrode assembly configured to both sense from and stimulate the nerve.

* * * * *